United States Patent [19]

Bencsits

[11] Patent Number: 5,589,181
[45] Date of Patent: Dec. 31, 1996

[54] INSECT REPELLENT

[75] Inventor: Franz Bencsits, Wehrenbachhalde 54, 8053 Zürich, Switzerland

[73] Assignees: Franz Bencsits; Perycut-Chemie AG, both of Switzerland

[21] Appl. No.: 290,991

[22] PCT Filed: Feb. 24, 1993

[86] PCT No.: PCT/EP93/00427

§ 371 Date: Nov. 23, 1994

§ 102(e) Date: Nov. 23, 1994

[87] PCT Pub. No.: WO93/16594

PCT Pub. Date: Sep. 2, 1993

[30] Foreign Application Priority Data

Feb. 27, 1992 [DE] Germany .................... 42 06 090.7

[51] Int. Cl.$^6$ .................................... A01N 25/02
[52] U.S. Cl. .................... 424/405; 424/DIG. 10; 514/519; 514/546; 514/549; 514/724
[58] Field of Search ................. 424/405, DIG. 10; 514/546, 549, 557, 558, 919, 324

[56] References Cited

U.S. PATENT DOCUMENTS

| | | | |
|---|---|---|---|
| 2,254,665 | 9/1941 | Ralston et al. | 424/405 |
| 2,396,012 | 5/1946 | Jones et al. | 424/405 |
| 3,340,040 | 9/1967 | Tso | 424/405 |
| 4,147,800 | 4/1979 | Singer et al. | 424/312 |
| 5,109,022 | 4/1992 | Jeanne et al. | 514/552 |

FOREIGN PATENT DOCUMENTS

| | | |
|---|---|---|
| 0045280 | 7/1981 | European Pat. Off. . |
| 0392806A1 | 10/1990 | European Pat. Off. . |
| 2190362 | 6/1972 | France . |
| 2235644 | 7/1974 | France . |
| 2377154 | 8/1978 | France . |
| 2665610 | 8/1990 | France . |
| 1931293 | 1/1970 | Germany . |
| 2530584 | 1/1977 | Germany . |
| 2801646 | 7/1978 | Germany . |
| 4012224 | 10/1991 | Germany . |
| 41-10040 | 5/1966 | Japan . |
| WO92/02138 | 2/1992 | WIPO . |

OTHER PUBLICATIONS

"Aliphatic monocarboxylic esters as insect repellents and attractants", Shulov et. al., Chemical Abstracts, vol. 82, No. 19, (1974).
"Controlling agent for wool harmful insects", Database WPIL, Week 8315, Derwent Publications Ltd., AN 83–36014K & JP,A,58 039 604, Mar. 08, 1983.
"Repellent for clothes moths, etc.", Database WPIL, Week 8315, Derwent Publications Ltd., AN 83–36013K & JP,A,58 039 603, Mar. 08, 1983.
"Moth repellent in orchards", Database WPIL, Derwent Publications Ltd., Week 7526, AN 75–43302W & JP,A,49 102 836, Sep. 28, 1974.
"Topical Insect Repellents", Soap Perfumery and Cosmetics, vol. 49, No. 2, p. 43, Feb. 1976.

"Hormone bis Keramik," Ullmans Encyklopädie der technischen Chemie, 1977, Band 13, pp. 237–238.
"Seife–Öl–Fette–Wachse", 110 (1984), pp. 297–300.
"Deutsche Apotheke Zeitung," 122/30 (1982), pp. 1539–2543.
"Pflegekosmetik–Ein Leitfaden," W. Raab, U. Kindl, Gustav Fischer Verlag, Stuttgart/New York 1991, pp. 159–160.
Rutledge et al., Chemical Abstracts, vol. 98, 1983, #84842h.
Knyazeva et al., Chemical Abstracts, vol. 81, 1974, #164791g.
"Investigations of repellents for protection against mosquitoes in Alaska", 1953. Robert J. Altman et al., Pesticides, vol. 13/No. 24, 1989, p. 1955.
"Plant insecticides. 9. Volatile constituents from Crotalaria ochroleuca and their effect on pest insects", Bestmann et al., Plant Biochem . . . , vol. 115, 1991, pp. 465–466.
"Identification of organic pollutants in the smoke from burning mosquito repellent by HPCGC–MS, Res. Cent. Eco–Environ. Sci.", Beijing, Peoples Rep. of China, Air Pollution, Ind. Hyg., vol. 112, 1990, p. 259.
"Bath Composition", T. K. Blond et al., Agrochemicals, vol. 103, 1985, p. 299.
"Mosquito repellents containing insecticides and cumarin as enhancer", Jingting Chen et al., Agrochemicals, vol. 116, 1992, p. 209.
"Field studies of the responses of tsetse flies (Glossinidae) and other Diptera to carbon dioxide, acetone and other chemicals", G. A. Vale, Chem. Abstracts, vol. 94, 1981, p. 254.
"Aromatic products as deodorants for insecticides and repellents", I. G. Kamorzina et al., Pesticides, vol. 66, 1967, p. 175.
"Repellent additives to reduce pesticide hazards to honeybees", E. L. Atkins et al., Agrochemicals, vol. 84, 1976, p. 131.
"Terpene derivatives as arthropod repellents", Walborg Thorsell et al., Chem. Abstracts, vol. 116, 1992, p. 328.
"Attractancy and repellency of alkyl carbonyl compounds for mosquito oviposition", T. Ikeshoji et al., Agrochemicals, vol. 87, 1977, p. 139.
"Ovipositional repellency of fatty acids and their derivatives against Culex and Aedes mosquitoes", Yih Shen Hwang et al., Chem. Abstracts, vol. 96, 1982, p. 316.
"Biological potency of synthetic fatty esters as insect scents to Tribolium castaneum (Herbst) and Trogoderma granarium (Everts)", John Pereira et al., Agrochemicals, vol. 106, 1987, p. 267.

(List continued on next page.)

Primary Examiner—Neil Levy
Attorney, Agent, or Firm—Finnegan, Henderson, Farabow, Garrett & Dunner, L.L.P.

[57] ABSTRACT

The invention relates to an insect repellent which contains at least one fatty acid alkyl ester having 1 to 4 carbon atoms in the alkyl group and at least one natural, nature-identical or synthetic fatty alcohol as the active substance and at least one natural or nature-identical vegetal or animal fatty oil as the carrier. The insect repellent serves for repelling flying, biting and sucking insects in man and beast and is applied onto the skin.

16 Claims, No Drawings

OTHER PUBLICATIONS

"Fatty acid esters for wool insects control", Agency of Industrial Sciences and Technology, Jpn., *Agrochemicals*, vol. 98, 1983, p. 219.

"Identification of ant repellent allomone produced by social wasp *Polistes fuscatus* (Hymenoptera:Vespidae)", D. C. Post et al., *Agrochemicals*, vol. 102, 1985, p. 191.

"Olfactory behavior of red flour beetle *Tribolium castaneum* (Herbst) (Coleoptera, Tenebrionidae) towards natural fatty acid esters", K. Singh et al., *Chem. Abstracts*, vol. 103, 1985, p. 156.

"Aliphatic monocarboxylic esters as insect repellents and attractants", Aharon Shulov et al, *Chem. Abstracts*, vol. 82, 1975, p. 138.

"Animal repellent composition", Janos Gyore et al., *Fertilizers, Soils, and Plant Nutrition*, vol. 74, 1971, p. 255.

"Identification of organic pollutants in the smoke from burning mosquito repellent by HPCGC–MS", Xiufen Liu et al., *Air Pollution, Inc. Hyg.*, vol. 112, 1990, p. 259.

"Aliphatic Monocarboxylic Esters as Insect Repellants and Attractants", by Aharon Shulov et al., Yissum Research Development Company of the Hebrew University of Jerusalem, (1974).

"Harry's Cosmeticology", Seventh Edition, Sep. 7, 1982, p. 214.

INSECT REPELLENT

The present invention relates to an insect repellent against flying, biting and sucking insects.

Repellents are chemical substances having a repellent effect on insects. Their use in human and veterinary hygiene is of great practical importance, where they protect man and beast against attack by bloodsucking, biting or otherwise annoying insects. It is required that repellents which are directly applied onto the skin are well tolerated by the skin, non-toxic, perspiration-resistant and light-fast and perfect in cosmetic respect. Moreover, the protection of the treated skin areas is to last for the longest possible period of time and the spectrum of activity of the repellents is to be as broad as possible, i.e. they should act against the largest possible number of harmful and annoying insects.

In the past, essential oils such as citronella oil, camphor and eucalyptus oil have been used as repellents; however, due to their disadvantages they were predominantly replaced by synthetic repellents. Synthetic repellents used in the prior art are e.g. phthalic acid dimethyl ester, 1,2-ethyl hexane-1,3-diol, 3,4-dihydro-2,2-dimethyl-4-oxo-2H-pyran-6-carboxylic acid-n-butyl ester, succinic acid dipropyl ester, N,N-diethyl-3-methyl-benzoic acid amide and pyridine-2,5-dicarboxylic acid-d-n-propyl ester (Ullmanns Encyklopädie der technischen Chemie, 4th edition, vol. 13, pages 237 et seq., 1977). However, such synthetic repellents are often not perspiration-resistant and irritate the mucous membranes. Skin tolerance and, more recently, also bio-degradability of each synthetic repellent must at first be examined.

Accordingly, the present invention is based on the object of providing an effective repellent for application onto the skin on the basis of natural and nature-identical raw materials with the least toxicological risk, which also develops a high effectiveness over a long period of time.

According to the invention, this object is attained by a repellent which contains at least one fatty acid alkyl ester having 1 to 4 carbon atoms in the alkyl group and at least one natural, nature-identical or synthetic fatty alcohol as the active substance and at least one natural or nature-identical vegetable or animal fatty oil as the carrier.

Moreover, the present invention relates to the use of the repellent according to the invention for repelling flying, biting and sucking insects in man and beast.

Examples for the fatty acid alkyl esters having 1 to 4 carbon atoms in the alkyl group, which are used in the insect repellent according to the invention are methyl, ethyl or butyl esters of fatty acids from natural or nature-identical vegetal or animal fatty oils from the group consisting of rape-seed oil, sunflower oil, peanut oil, peanut butter, soy oil, safflower seed oil, cuphea oil, coconut oil, palm kernel oil, palm oil and fish oil. Fatty acids having 5 to 19 carbon atoms are preferred.

A natural, nature-identical or synthetic fatty alcohol having preferably 5 to 18 carbon atoms, being saturated or having 1 to 3 unsaturated bonds per molecule is admixed to the used fatty acid alkyl ester as a further active substance according to the invention. The natural fatty alcohols are e.g. obtained from vegetal and/or animal oils and/or the fatty acids and/or fatty acid alkyl esters, which can be obtained therefrom. The nature-identical and/or synthetic fatty alcohols can e.g. be obtained from paraffin and/or ethene. A preferred active substance combination of the repellent according to the invention contains 1 to 99% by weight of the fatty acid alkyl ester and 99 to 1% by weight of the fatty alcohol.

In further preferred embodiments, the repellent according to the invention contains 70 to 98% by weight of fatty acid alkyl ester and 30 to 2% by weight of fatty alcohol, 30 to 2% by weight of fatty acid alkyl ester and 70 to 98% by weight of fatty alcohol, 60 to 97% by weight of fatty acid alkyl ester and 40 to 3% by weight of fatty alcohol or 40 to 3% by weight of fatty acid alkyl ester and 60 to 97% by weight of fatty alcohol.

In order to slow down the evaporation of the active substance(s) and to achieve the effect over an especially long period of time due to this, at least one carrier from the group consisting of natural or nature-identical vegetal or animal fatty oils is added to the repellent according to the invention. Examples of the natural or nature-identical vegetal or animal fatty oils are rape-seed oil, sunflower oil, peanut oil, peanut butter, soy oil, safflower seed oil, cuphea oil, coconut oil, palm kernel oil, palm oil and fish oil.

At least one free fatty acid may be contained in the repellent according to the invention as an additional carrier. These are e.g. obtained by means of the hydrolytic decomposition of natural or nature-identical vegetal and/or animal oils and have preferably 5 to 19 carbon atoms in the chain. Examples are valeric acid, caproic acid, oenanthic acid, caprylic acid, pelargonic acid, capric acid, undecanoic acid, lauric acid, tridecanoic acid, myristic acid, pentadecanoic acid, palmitic acid, margaric acid, stearic acid and nonadecanoic acid and isovaleric acid, palmitoleic acid, oleic acid, sorbic acid, linolic acid, linolenic acid and elaeostearic acid.

An insect repellent containing 75 to 98% by weight of the fatty acid alkyl ester and 2 to 25% by weight of the fatty oil is also preferred. Moreover, an insect repellent is preferred, which contains 8 to 70% by weight of the fatty acid alkyl ester, 5 to 90% by weight of the fatty alcohol and 2 to 25% by weight of the fatty oil. A further preferred insect repellent contains 75 to 98% by weight of the fatty acid alkyl ester and 25 to 2% by weight of the free fatty acid or 1 to 97% by weight of the fatty acid alkyl ester, 1 to 97% by weight of the fatty alcohol and 2 to 25% by weight of the free fatty acid. Moreover, a preferred insect repellent comprises 1 to 96% by weight of the fatty acid alkyl ester, 2 to 25% by weight of the fatty oil and 2 to 25% by weight of the free fatty acid or 1 to 95% by weight of the fatty acid alkyl ester, 1 to 95% by weight of the fatty alcohol and respectively 2 to 25% by weight of the fatty oil or the free fatty acid. Rape seed oil is preferred as natural vegetal oil, which may e.g. be contained in an amount of 20% to 80% by weight of a first runnings coconut methyl ester in the insect repellent.

The fatty alcohols, fatty acid alkyl esters and fatty acids may be obtained by means of a simple chemical reaction from natural or nature-identical, toxicologically harmless raw materials, e.g. by means of hydrolysis, reesterification, hydrogenation, high-pressure hydrogenation, hardening and/or dehydration as known in the prior art. The fatty oils used according to the invention may also be obtained by means of conventional processes from oil-supplying materials such as plant seeds and animal fats. Accordingly, the insect repellent according to the invention contains one or several substances prepared from completely harmless, synthetic (nature-identical) basic substances or directly from natural basic substances, and, consequently, has the least toxicological and irritative risk with an excellent repelling effect. It is preferably used by applying it onto the skin of man and beast to repel flying, biting and sucking insects.

The following examples explain the invention.

1. Examples of insect repellents (I) 20% by weight of rape seed oil 20% by weight of coconut methyl ether (8 to 18 carbon atoms in the fatty acid radical) 50% by weight of first runnings coconut fatty alcohol ($C_8$ to $C_{10}$)

(II) 10% by weight of rape seed oil 10% by weight of first runnings coconut palm kernel fatty acid ($C_8$ to $C_{12}$) 35% by weight of coconut methyl ester (8 to 18 atoms in the fatty acid radical) 45% by weight of first runnings coconut fatty alcohol ($C_8$ to $C_{10}$)

(III) 30% by weight of rape seed methyl ester 5% by weight of soy methyl ester 10% by weight of sunflower methyl ester 5% by weight of coconut methyl ester 30% by weight of first runnings coconut methyl ester 15% by weight of first runnings palm kernel alcohol 5% by weight of rape seed oil 2. Application Examples The insect repellents (I) and (II) were tested with two different persons.

Test:

The forearm of a test subject was treated with the corresponding test substances (I) or (II) on an area of approx. 250 cm$^2$. The amount of 2 ml of the corresponding test substance was distributed uniformly. The treated forearm area was sealed at both ends with a mosquito-tight adhesive tape and a short plastic hose. The untreated hand was covered by a thick glove and, thus, served at the same time as a control for the biting activity of the test animals.

About 300 to 400 yellow fever mosquitoes (*Aedes aegypti*), almost exclusively females, were placed into a breeding cage measuring 40×40×40 cm.

The forearm and the hand were held into the mosquito cage for the test every hour, and, for 10 minutes, the number of mosquitos was recorded, which (a) attempted to bite through the glove (positive control),
(b) approached the treated area closer than 3 cm,
(c) remained seated on the treated area longer than 2 seconds, and
(d) bit the treated area and sucked blood.

Test substance (I) (Test subject (1))

| Time (h) | Glove a) | Approaching b) | Remaining seated c) | Biting d) |
|---|---|---|---|---|
| 1.5 | 100 | 33 | 14 | 0 |
| 2.5 | 100 | 27 | 12 | 0 |
| 4.0 | 100 | 45 | 37 | 0 |
| 5.0 | 100 | 26 | 5 | 0 |
| 6.5 | 100 | 46 | 30 | 0 |

Test substance (II) (Test subject (2))

| Time (h) | Glove a) | Approaching b) | Remaining seated c) | Biting d) |
|---|---|---|---|---|
| 1 | 160 | 51 | 17 | 0 |
| 2 | 130 | 50 | 27 | 0 |
| 3 | 100 | 50 | 5 | 0 |
| 4 | 100 | — | 17 | 0 |
| 5 | 100 | 24 | 13 | 0 |
| 6 | 100 | 63 | 36 | 0 |
| 7 | 100 | 99 | 62 | 0 |

The parameters a) and b) are estimated values since an exact determination is not possible.

The effectiveness of a substances results above all from the ratio of the mosquitoes, which are ready to bite and remain seated on the glove. The number of the biting mosquitoes is the decisive factor for the duration of the effect and, thus, in the tropics, indirectly also for the risk of infection. The tested substances ensure protection of more than 3 hours. As can be seen from the parameters b) and c) there is also a specific number of approaching mosquitoes and mosquitoes remaining seated if the substances according to the invention are used, however, they do not bite. Accordingly, a strong repellent effect can be attributed to all tested substances.

I claim:

1. An insect repellant consisting essentially of (a) an active substance combination of 1 to 99% by weight of at least one fatty acid alkyl ester having 1 to 4 carbon atoms in the alkyl group and 99 to 1% by weight of at least one natural, nature-identical or synthetic fatty alcohol having 5 to 18 carbon atoms in (b) a carrier of at least one natural or nature-identical normally liquid vegetal fatty oil selected from the group consisting of rape-seed oil, sunflower oil, peanut oil, soy oil, and coconut oil.

2. An insect repellant according to claim 1, wherein the repellant contains 75 to 98% by weight of the fatty acid alkyl ester and 2 to 25% by weight of the fatty oil.

3. An insect repellant according to claim 1, wherein the repellant contains 8 to 80% of the fatty acid alkyl ester, 5 to 90% by weight of the fatty alcohol and 2 to 25% by weight of the fatty oil.

4. An insect repellant according to claim 1, wherein the carrier also contains at least one free fatty acid.

5. An insect repellant according to claim 4, wherein the repellant contains 75 to 98% by weight of the fatty acid alkyl ester and 25 to 2% by weight of the free fatty acid.

6. An insect repellant according to claim 4, wherein the repellant contains 1 to 97% by weight of the fatty acid alkyl ester, 1 to 97% by weight of the fatty alcohol and 2 to 25% by weight of the free fatty acid.

7. An insect repellant according to claim 4, wherein the repellant contains 1 to 96% by weight of the fatty acid alkyl ester, 2 to 25% by weight of the fatty oil and 2 to 25% by weight of the free fatty acid.

8. An insect repellant according to claim 4, wherein the repellant contains 1 to 95% by weight of the fatty acid alkyl ester, 1 to 95% by weight of the fatty alcohol, 2 to 25% by weight of the fatty oil and 2 to 25% by weight of the free fatty acid.

9. An insect repellant according to claim 1, wherein the fatty acid alkyl ester is a methyl, ethyl or butyl ester of fatty acids from natural or nature-identical vegetal or animal fatty oils selected from the group consisting of rape-seed oil, sunflower oil, peanut oil, peanut butter, soy oil, safflower seed oil, cuphea oil, coconut oil, palm kernel oil, palm oil and fish oil.

10. An insect repellant according to claim 1, wherein the alcohol is a natural fatty alcohol obtained from vegetal or animal oils, or fatty acids or fatty acid alkyl esters obtained from said oils.

11. An insect repellant according to claim 1, wherein the nature-identical or synthetic fatty alcohols are obtained from paraffin or ethene.

12. An insect repellant according to claim 10, wherein the natural, nature-identical and synthetic fatty alcohols are saturated or have 1 to 3 unsaturated bonds per molecule.

13. An insect repellant according to claim 4, wherein the fatty acids are obtained by means of hydrolytic decomposition of natural or nature-identical vegetal or animal oils.

14. An insect repellant according to claim 13, wherein the fatty acids have 6 to 19 carbon atoms in the chain.

15. A method of repelling flying, biting and sucking insects, which comprises applying to a human or beast a repellant amount of the insect repellant of claim 1.

16. The method according to claim 15, wherein the insect repellant is applied onto the skin of the human or beast.

* * * * *